US00PP13519P2

(12) United States Plant Patent
Lemon

(10) Patent No.: US PP13,519 P2
(45) Date of Patent: Jan. 28, 2003

(54) GERANIUM PLANT NAMED 'JEWEL'

(75) Inventor: David Lemon, County of Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/877,168

(22) Filed: Jun. 8, 2001

(51) Int. Cl.[7] ..... A01H 5/00

(52) U.S. Cl. ..... Plt./331

(58) Field of Search ..... Plt./331

*Primary Examiner*—Bruce R. Campell
*Assistant Examiner*—A Para
(74) *Attorney, Agent, or Firm*—Webb Ziesenheim Logsdon Orkin Hanson, P.C.

(57) ABSTRACT

A new and distinct early flowering regal geranium plant with white petals having a blotch of red-purple in the center and red-purple veining above medium green foliage.

1 Drawing Sheet

CLASSIFICATION

*Pelargonium×domesticum* (regal geranium).

VARIETAL DENOMINATION

'Jewel'.

BACKGROUND OF THE INVENTION

The present invention comprises a new and distinct cultivar of *Pelargonium×domesticum* known by the varietal name 'Jewel'. The new variety was discovered in a selected breeding program in Lompoc, Calif. The new variety is a selection from the cross of unpatented proprietary breed variety Seedling Purple Bicolor #607, the female parent and 'Lois' (U.S. Plant Pat. No. 10,000), the male parent. The new variety is more compact than 'Lois'. The new variety was first asexually reproduced by cuttings in Connellsville, Pa. The new variety has been trial and field tested and has been found to retain its distinctive characteristics and remain true to type through successive propagations.

The cultivar, when grown in a glass greenhouse in Connellsville, Pa. using natural light and temperatures of 60° F. night and 68° F. day, has a response time of 13 weeks from a rooted cutting to flowering in a 6 inch pot. The response time was determined on plants grown in soilless media employing constant fertilizer 150–200 parts per million of nitrogen and potassium in full light.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar at 10 weeks grown from a rotted cutting. The data which defines these characteristics were collected by asexual reproductions carried out by Oglevee, Ltd. in Connellsville, Pa. The color readings were taken on a plant under 200–220 foot candles of fluorescent cool white light. Color references are primarily to The R.H.S. Colour Chart of The Royal Horticultural Society of London.

PLANT

Form: Medium mound.
Height: 19–21 cm from soil to top of foliage.
Growth: Upright, free basal branching.
Strength: Does not require artificial support.
Foliage: Stalked leaf attachment; medium green foliage.
Rooting time: Roots visible to outside of artificial dirt plug in 14–21 days.
Leaves:
- *Size.*—Length: 5–8.5 cm. Width: 9–11 cm.
- *Shape.*—Reniform; truncate base.
- *Margin.*—Serrated; lobed.
- *Texture.*—Leathery; pubescent.
- *Color.*—Upper surface: Green Group 137A. Lower surface: Green Group 138A.
- *Ribs and veins.*—Venation: Palmate. Color: Green Group 138C fading to Green Group 138A.

Petioles:
- *Color.*—Yellow-Green Group 144A.
- *Length.*—7.5–9.1 cm.

Stem:
- *Color.*—Yellow-Green Group 144A.
- *Internode length.*—1.2–2.8 cm.

THE BUD

Shape:
- *Overall.*—Elliptical to round cluster.
- *Individual bud.*—Elliptical.

Size:
- *Overall.*—4–6.5 cm across.
- *Individual bud.*—2.4–2.9 cm long; 0.9–1.2 cm wide.

Number of buds per cluster: 7–10.

INFLORESCENCE

Blooming habit: Continuous; large florets forming full flower heads.
- *Size.*—11–14 cm.
- *Borne.*—Flowers on umbel; umbel on pedicel; pedicel on peduncle.

Flowers:
- *Form.*—Opened to slightly cupped; petals overlap; slightly ruffled.
- *Number of flowers per umbel.*—7–10.

*Size.*—Diameter: 6–7.5 cm. Depth: 3–4.5 cm.

*Petals.*—Color: Upper surface: Lower Petals: White Group 155C. A blotch of Red-Purple Group 61B is present in the center of the lower petal with a diameter of 1.4–1.6 cm fading at the edge of the blotch to Red-Purple Group 61C. The veining in the blotch is darker Red-Purple Group 61A. There is a distinct veining on the upper surface of the lower petal of Red-Purple Group 61B fading into white at the edge of the petal. Upper Petals: Base and outer edge are White Group 155D. The majority of the upper petal is Red-Purple Group 59A changing into Red-Purple Group 61A and fading into Red-Purple Group 61C then into white at the edge. Towards the center and base of the petal the color changed to Red-Purple Group 64B and then into White Group 155D at the base of the petal. The veins start white at the base and then change into Red-Purple Group 61A and Greyed-Purple Group 187B in the center of the petal. Lower surface: Lower Petals: The petals are White Group 155D. In the center where the blotch is on the upper surface, there is some Red-Purple Group 57C shining through. The veins are shining through in Purple Group 76C. Upper Petals: Base and outer edge are White Group 155D. There is a big eye in the center of Red-Purple Group 59A fading into Red-Purple Group 61A and Red-Purple Group 61B. The veins start White Group 155D at the base and change into Red-Purple Group 59B. Shape: Obovate. Size: Length: 4.6–5.2 cm. Width: 3.2–4.8 cm. Margin: Entire. Number per floret: 5.

Texture and appearance: Smooth, satiny, velvety.

Tonality from a distance: Deep purple shiny upper petals in contrast to the much brighter with more white, lower petals, above medium green foliage.

Petaloids: None observed.

Pedicel:

*Length.*—2–2.3 cm.

*Color.*—Yellow-Green Group 144A.

Peduncle:

*Length.*—7–8.5 cm.

*Color.*—Yellow-Green Group 144A.

Disease/pest resistance: No unusual susceptibility to diseases or pests has been noted to date.

Lasting quality: Individual umbels will last in the home environment for 4–6 weeks. Overall flowering will continue as long as conditions remain cool at night with plenty of light provided.

Fragrance: None.

REPRODUCTIVE ORGANS

Stamens:

*Quantity.*—7.

*Anthers.*—3–4 mm.

*Filaments.*—Length: 1.6–2 cm. Color: White. Pollen: Golden orange.

Pistils:

*Number.*—One.

*Length.*—1.6–2 cm.

*Stigma.*—Number: One; five or six parted. Color: Greyed-Purple Group 187B.

*Style.*—Length: 15–18 mm. Color: Greyed-Purple Group 187C.

Ovaries:

*Completeness.*—Superior.

*Pubescence.*—Greatly pubescent.

*Length.*—5–7 mm.

*Width.*—3 mm.

*Color.*—Yellow-Green Group 147C.

Fruit: None observed.

GENERAL CHARACTERISTICS

1. 'Jewel' has unique coloring.
2. Controlled plant type.
3. Very free flowering.

I claim:

1. A new and distinct variety of geranium plant substantially as shown and described.

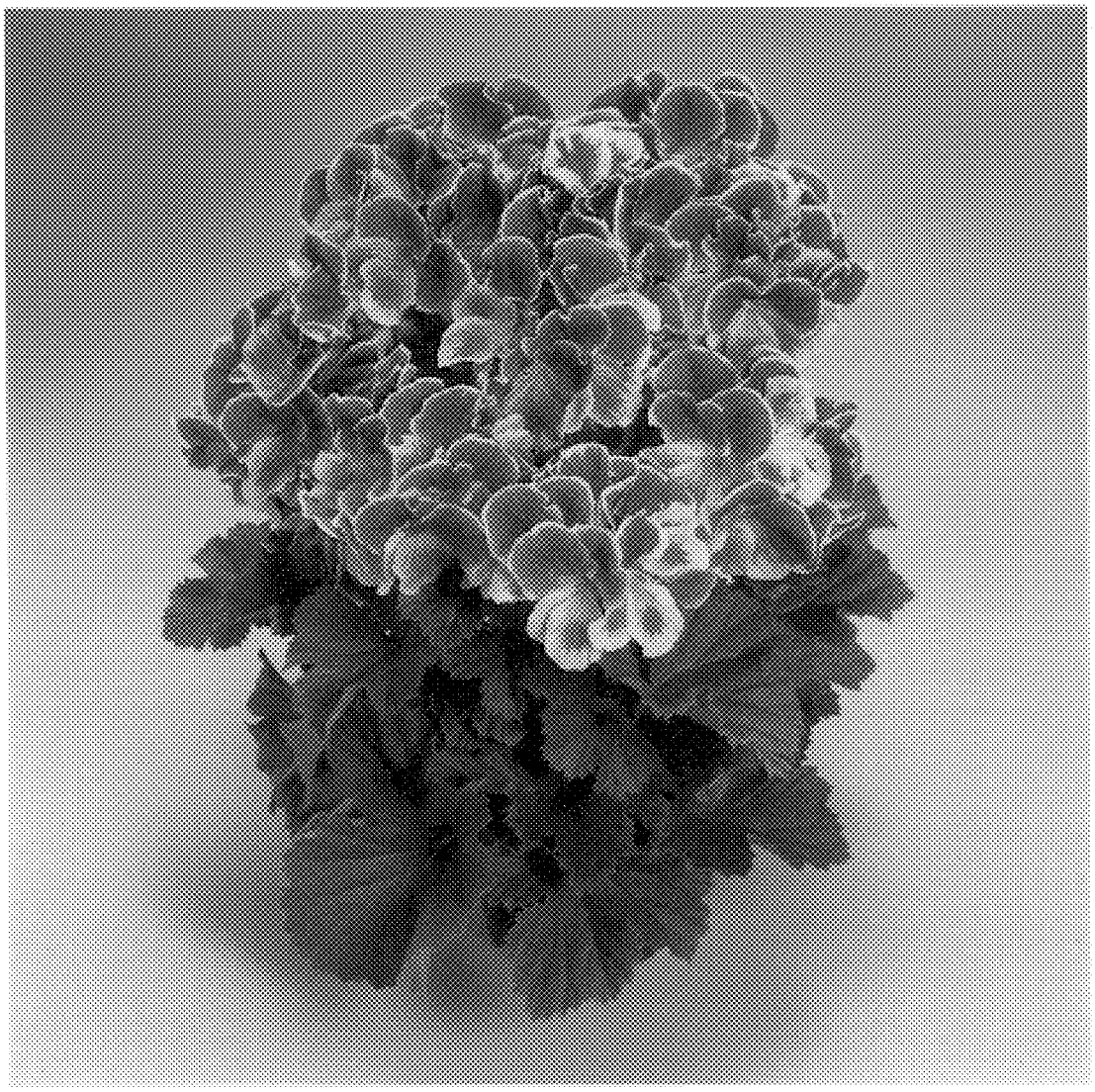

* * * * *